United States Patent [19]
Rader et al.

[11] Patent Number: 5,793,478
[45] Date of Patent: Aug. 11, 1998

[54] APPARATUS FOR MEASURING PARTICLE PROPERTIES

[75] Inventors: Daniel J. Rader; Jaime N. Castaneda; Thomas W. Grasser; John E. Brockmann, all of Albuquerque, N. Mex.

[73] Assignee: Sandia Corporation, Albuquerque, N. Mex.

[21] Appl. No.: 752,337

[22] Filed: Nov. 19, 1996

[51] Int. Cl.$^6$ .............................. G01P 3/36; G01N 21/00
[52] U.S. Cl. .................. 356/28; 356/336; 356/338; 356/342
[58] Field of Search ............ 356/28, 342, 335–338

[56] References Cited

U.S. PATENT DOCUMENTS

| | | | |
|---|---|---|---|
| 4,251,733 | 2/1981 | Hirlemann, Jr. | 250/575 |
| 4,387,993 | 6/1983 | Adrian | 356/336 |
| 4,636,075 | 1/1987 | Knollenberg | 356/336 |
| 4,707,130 | 11/1987 | Hofmann et al. | 356/28 |
| 4,840,486 | 6/1989 | Schodl | 356/338 |
| 4,851,697 | 7/1989 | Schodl | 356/28 |
| 4,854,705 | 8/1989 | Bachalo | 356/336 |
| 4,859,055 | 8/1989 | Gal | 356/28 |

*Primary Examiner*—Stephen C. Buczinski
*Attorney, Agent, or Firm*—V. Gerald Grafe

[57] ABSTRACT

An apparatus for determining particle properties from detected light scattered by the particles. The apparatus uses a light beam with novel intensity characteristics to discriminate between particles that pass through the beam and those that pass through an edge of the beam. The apparatus can also discriminate between light scattered by one particle and light scattered by multiple particles. The particle's size can be determined from the intensity of the light scattered. The particle's velocity can be determined from the elapsed time between various intensities of the light scattered.

19 Claims, 4 Drawing Sheets

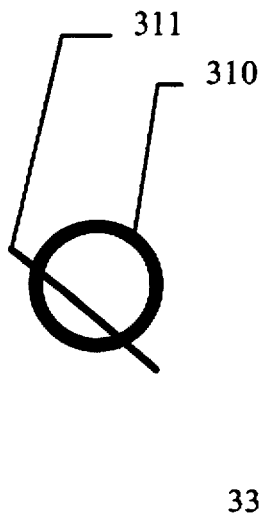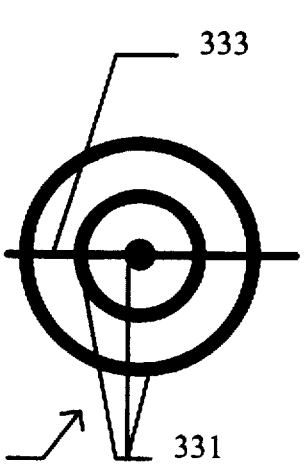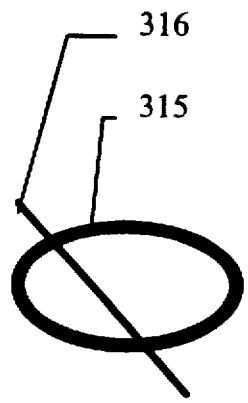
Figure 3a    Figure 3b    Figure 3c
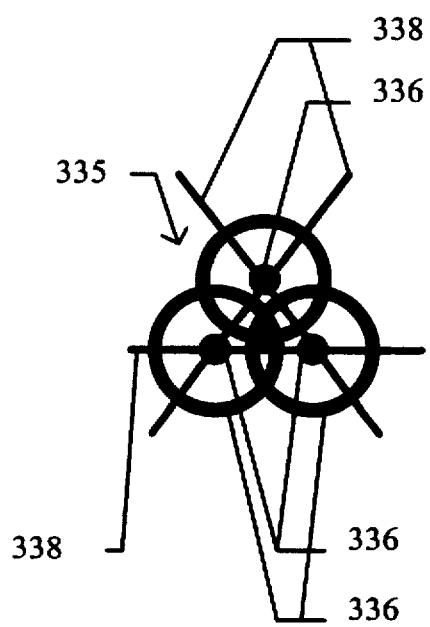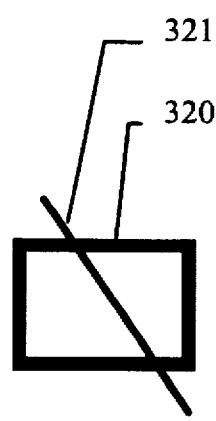
Figure 3d    Figure 3e

1

APPARATUS FOR MEASURING PARTICLE PROPERTIES

This invention was made with Government support under Contract DE-AC04-94AL85000 awarded by the U.S. Department of Energy. The Government has certain rights in the invention.

BACKGROUND OF THE INVENTION

The present invention relates to the measurement of particle properties, and more specifically to the measurement of aerosol particle flux, size and velocity.

The characterization of airborne particles and droplets is critical in the study of a wide range of fields, including combustion, environment, industrial processing, clean-room monitoring, and cloud and fog formulation. The distributions of particle size, shape, structure, charge, chemical composition, and velocity are each important.

Extractive particle measurement systems remove a sample from the volume and measure the properties of the sample. Removing the sample risks biasing the properties of interest. In situ particle measurement systems, on the other hand, measure the properties of the particles in the original volume and therefore do not risk biasing the properties of interest. In situ particle measurement systems are currently available commercially. Examples include: the FSSP models from Particle Measuring Systems, Inc., of Boulder, Colo., the HC series particle sizers from Polytec Optronics of Costa Mesa, Calif., the PCSV system from Insitec Measurement Systems of San Ramon, Calif., and the TPM system from High Yield Technology of Sunnyvale, Calif.

Many particle measurement systems, including the commercial systems mentioned above, are based on laser illumination and particle light scattering. Some systems can not measure single particle properties and can only provide ensemble measurements. See, e.g., Wotling, U.S. Pat. No. 4,975,237; Dixon, U.S. Pat. No. 3,873,206. Some systems characterize particles based on their random Brownian motion, typically effective only for small particles. See, e.g., Hutchins and Dahneke, U.S. Pat. No. 5,502,561; Hutchins and Dahneke, U.S. Pat. No. 5,434,667. Others use laser doppler velocimetry or phase doppler velocimetry and consequently require very complex apparatus. See, e.g., Carr, Clarke, and Al-Shukri, U.S. Pat. No. 5,160,976; Brown, U.S. Pat. No. 4,925,297; Buchhave, Knuhtsen and Olldag, U.S. Pat. No. 4,701,051; Bachalo, U.S. Pat. No. 4,986,659. Others use light scattering from individual particles, allowing single particle measurement without the complexity of the doppler systems. See, e.g., Gal and Morrow, U.S. Pat. No. 4,859,055; Bachalo, U.S. Pat. No. 4,854,705; Adrian, U.S. Pat. No. 4,387,993; Hirleman, U.S. Pat. No. 4,251,733; Knollenburg, U.S. Pat. No. 4,636,075. As discussed below, currently known single beam, single particle measurement systems can not accurately measure a single particle's size and velocity because the particle path through the laser beam is unknown. TSI Incorporated has described a system using overlapping parallel laser beams in an attempt to overcome this problem at the expense of doubling the laser and detection systems. APS 3320 Advance Product Information, TSI Incorporated, St. Paul, Minn.

FIG. 1 shows the structure of a representative single particle measurement system. A laser 101 is focused by a first lens 102 into a sample volume V. Particles crossing the light beam, such as particle P, scatter light. Part of the scattered light is focused by a second lens 103 through a spatial filter 104 onto a detector 105. The detector 105 converts the scattered light received into an electrical signal. Particle size is related to the peak intensity of the scattered light. Particle velocity is related to the time the particle spends in the light beam, and is therefore related to the duration of the light scattering event.

Laser beams typically have a Gaussian intensity cross section (at an angle to the beam propagation axis), with the maximum intensity at the center of the light beam and intensity decaying asymptotically toward zero with increasing radial distance from the center. A particle passing through the center of a Gaussian laser beam will scatter more light over a longer period of time than the same sized particle passing near the edge of a Gaussian laser beam. A small particle passing through the center of a Gaussian laser beam can produce a similar scattered light pattern as a large particle passing near the edge of a Gaussian laser beam. Since the scattered light intensity and duration are both dependent on the particle's unknown trajectory, accurate measurement of a single particle's size and velocity are not possible. Measurement of a large number of particles can provide the input to a statistical deconvolution to deduce the particle size and velocity distributions. However, this technique is complex, and limits the utility of present systems: it is impossible to correlate particle size and velocity, either high particle concentration s or long measurement times are needed to capture a statistically significant number of scattering events, and the deconvolution leads to additional uncertainties in the measurements.

One attempt to overcome the trajectory problem employs two laser beams: a large main beam for light scattering and a smaller pointer beam for determining when a particle has crossed near the center of the large beam. See, e.g., Adrian, U.S. Pat. No. 4,387,993. This technique limits the measurement to particles that cross both beams. The generation of two confocal light beams can be very complex, increasing the cost and decreasing the reliability of pointer beam systems. Detection apparatus capable of detecting and distinguishing between the two beams without interference is more complex, and consequently more expensive and less reliable, than that required for single beam systems.

Accordingly, there is a need for an apparatus that can measure single particle properties without generating erroneous determinations based on particle trajectory and without the added complexity of dual laser beams and dual detection systems.

SUMMARY OF THE INVENTION

The present invention uses a light beam with particular intensity characteristics to determine the properties of particles passing through the light beam. The invention comprises means for generating a light beam, means for directing the light beam into the path of the particle, means for detecting light scattered by the particle, and means for analyzing the scattered light to determine particle properties. The light beam has an intensity cross section designed so that particles passing through the light beam cross an area of high intensity, then one of low intensity, then another of high intensity. The light scattered by a particle passing through such a light beam has a distinctive multi-humped intensity profile. Particles passing through the edge of the light beam and coincident particles (more than one particle in the sample volume at the same time) do not generate the distinctive profile and therefore can be rejected to avoid erroneous measurements.

A laser beam with an annular cross section can provide a suitable intensity cross section. The intensity at the center of the beam is nonzero and less than the intensity at a selected radial distance from the center. Multiple parallel beams and other single beam cross sections can also provide suitable intensity cross sections.

The particle flux can be determined from the number of distinctive scattering profiles detected during a suitable time interval. The particle size can be determined from the maximum scattered light intensity. The particle velocity can be determined from the elapsed time between the two scattered light maxima, the elapsed time between detections of scattered light of a selected proportion of the maximum scattered light intensity, and the physical characteristics of the light beam.

Additional objects, advantages, and novel features will become apparent to those skilled in the art upon examination of the following description or may be learned by practice of the invention. The objects and advantages of the invention may be realized and attained by means of the instrumentalities and combinations particularly pointed out in the appended claims.

DESCRIPTION OF THE FIGURES

The accompanying drawings, which are incorporated into and form part of the specification, illustrate an embodiment of the invention and, together with the description, serve to explain the principles of the invention.

FIGS. 3(a,b,c,d,e) show representative light beam intensity cross sections according to the present invention.

DETAILED DESCRIPTION OF THE INVENTION

The present invention provides an improvement to present particle property measurement systems. Using a light beam with specific intensity cross section allows discrimination between particles crossing enough of the light beam to provide a reliable particle property determination and those crossing only the fringes of the light beam. The analysis uses the characteristics of the light beam and of the scattered light to determine particle properties, for example particle flux and individual particle size and velocity, more accurately and simply than possible with present systems.

Figure 1:
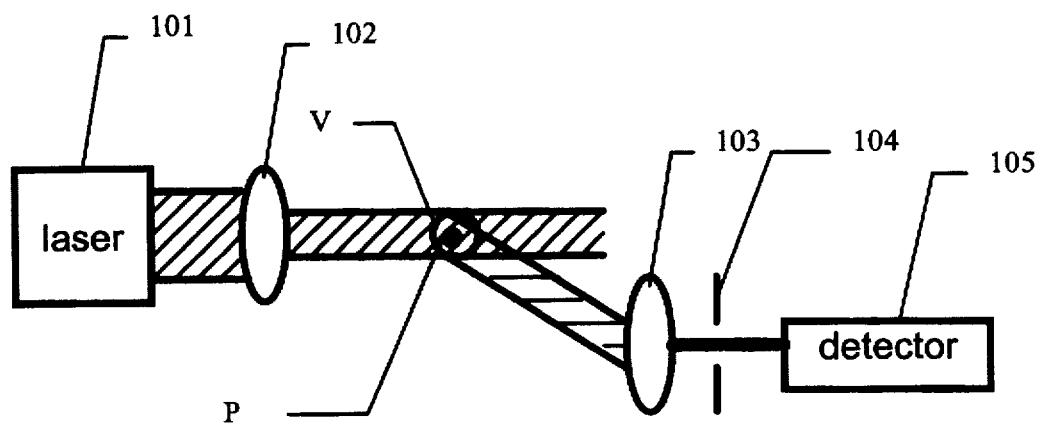
FIG. 1 shows prior art particle property determination apparatus.
Figure 2:
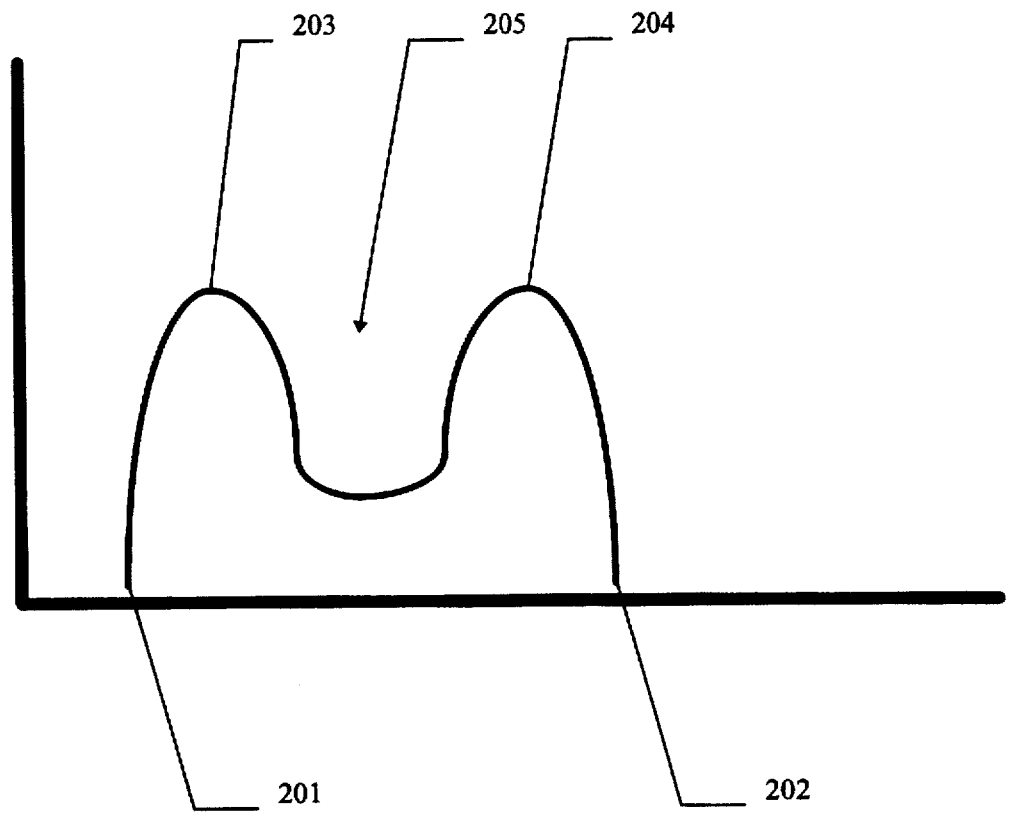
FIG. 2 shows the beam intensity profile of a light beam according to the present invention.

The present invention uses a light beam with an intensity cross section along a particle path as shown in FIG. 2. The beam has edges where the intensity drops to a minimum 201, 202. Between the beam edges the beam intensity rises to a higher value at two other points 203, 204 along the particle path. The valley 205 between the two peaks 203, 204 has a nonzero intensity that is less than the intensity at the two peaks 203, 204.

The intensity profile described in FIG. 2 can be achieved in many ways. Several suitable light beam cross sections are shown in FIGS. 3(a,b,c,d,e). Those skilled in the art will appreciate that other arrangements and shapes can also provide the required beam intensity characteristics. Annular cross section light beam 310 has a ring of higher intensity surrounding a lower intensity inner region. Particles crossing the ring, such as on path 311, will encounter the desired intensity pattern. Elliptical light beam 315 has an elliptical ring of higher intensity surrounding a lower intensity inner region. Particles crossing the elliptical ring, such as on path 316 will encounter the desired intensity pattern.

Polygonal light beam 320 has a perimeter of high intensity surrounding a lower intensity region. Particles crossing the perimeter, such as on path 321, will encounter the desired intensity pattern.

Bullseye light beam 330 has multiple concentric high intensity regions 331. A particle with path 333 will encounter the desired intensity pattern as it travels through the high intensity regions 331 and the intermediate lower intensity regions. The resulting scattered light intensity can have multiple peaks, corresponding to the multiple high intensity regions encountered by the particle.

Triple light beam 335 has three high intensity spots 336. A particle on any of the paths 338 will encounter the desired intensity pattern as it crosses the high intensity spots 336 and the intermediate lower intensity regions 337.

Light beams with suitable intensity characteristics can be made in several ways. For example, lasers can generate a suitable light beam. An optical fiber mounted with the laser so that the laser beam propagation axis is not parallel to the fiber axis can produce an annular beam. Metal on glass or other masking means can produce annular, bullseye, and polygonal beams. Multiple lasers can produce multiple intensity beams such as a triple light beam. Lenses and prisms can be used in various combinations that will be apparent to those skilled in the art to produce light beams with suitable intensity cross sections.

Figure 4A:
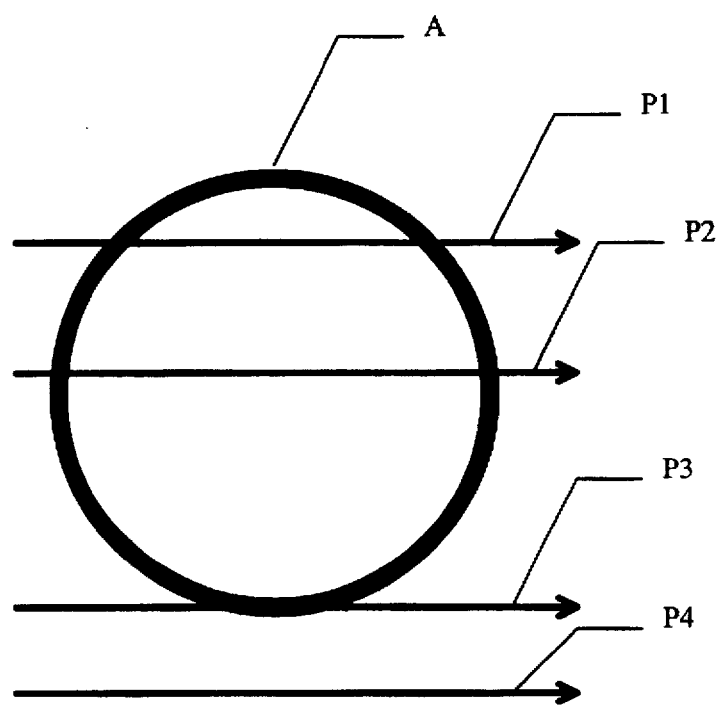
FIGS. 4(a,b) show possible particle paths through a light beam according to the present invention and corresponding detected scattered light.
Figure 4B:
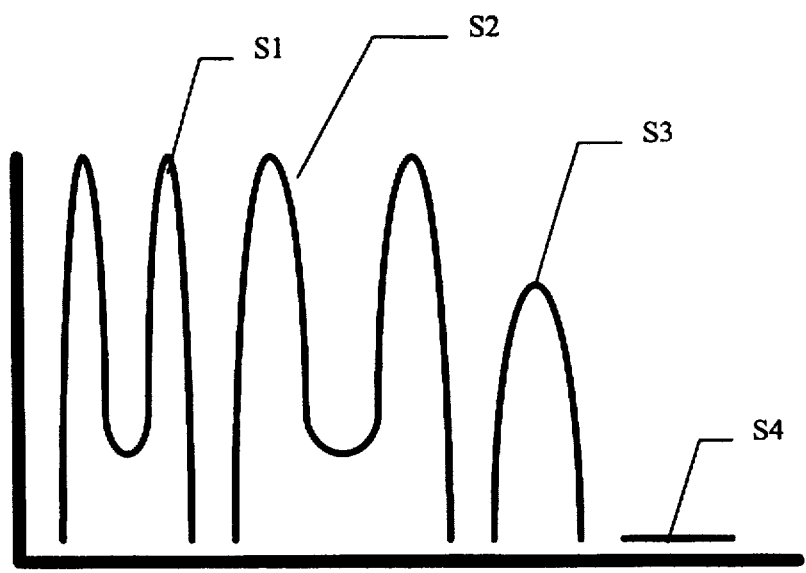

FIG. 4a shows several possible particle paths across an annular light beam A; FIG. 4b shows the corresponding intensity of the light scattered by a particle as it traverses the path. A particle on path P1 in FIG. 4a scatters light from the high intensity annular region and from the lower intensity inner region. The scattered light can be collected by means such as a photodetector. The corresponding scattering pattern S1 in FIG. 4b shows higher intensity when the particle passes through the high intensity annular region and reduced intensity when the particle passes through the lower intensity inner region. The scattering drops to zero as the particle passes out of the beam. A particle with the same velocity traveling path P2 in FIG. 4a shows a similar scattering pattern S2 in FIG. 4b, except that the two high intensity scattering points can be farther apart in time because the path includes more of the lower intensity inner region. A particle on path P3 in FIG. 4a scatters light only from one encounter with the high intensity annular region. The corresponding scattering pattern S3 in FIG. 4b shows a single peak. A particle on path P4 in FIG. 4a does not encounter the beam and consequently shows a flat scattering pattern S4 in FIG. 4b.

As the scattering patterns illustrate, particles that cross the high intensity annular region and penetrate the lower intensity inner region generate a scattering pattern with two peaks. Particles that cross only one edge of the high intensity annular region will generate only one peak. Two particles crossing just the edge of the high intensity annular region usually will not generate the reduced, but nonzero, scattering between the two peaks.

Two particles crossing just the edge of the high intensity annular region might generate a two peak pattern, but the peaks in general will not have the same intensity relationship as the peaks from a single particle. Accordingly, any scattering pattern that shows twin peaks with a selected intensity relationship surrounding a reduced but nonzero inner region indicates a single particle crossing the beam. For angularly symmetric beams, the two peaks will have substantially equal intensity. The determination of particle properties can be based on only scattering events with appropriate intensity profiles since they indicate that a single particle has passed through known regions of the beam. For example, the particle flux through the sample volume can be determined from the number of scattering events with appropriate intensity profiles in a selected time interval.

Figure 5A:
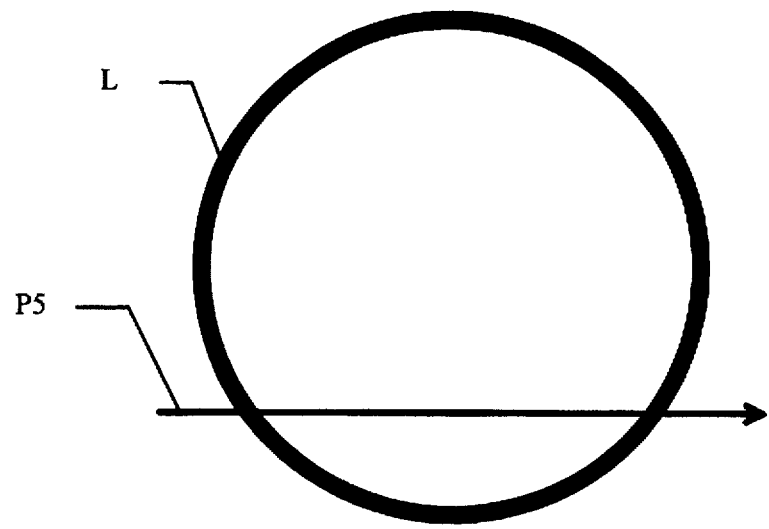
FIGS. 5(a,b) shows a particle path through a light beam according to the present invention and corresponding detected scattered light.
Figure 5B:
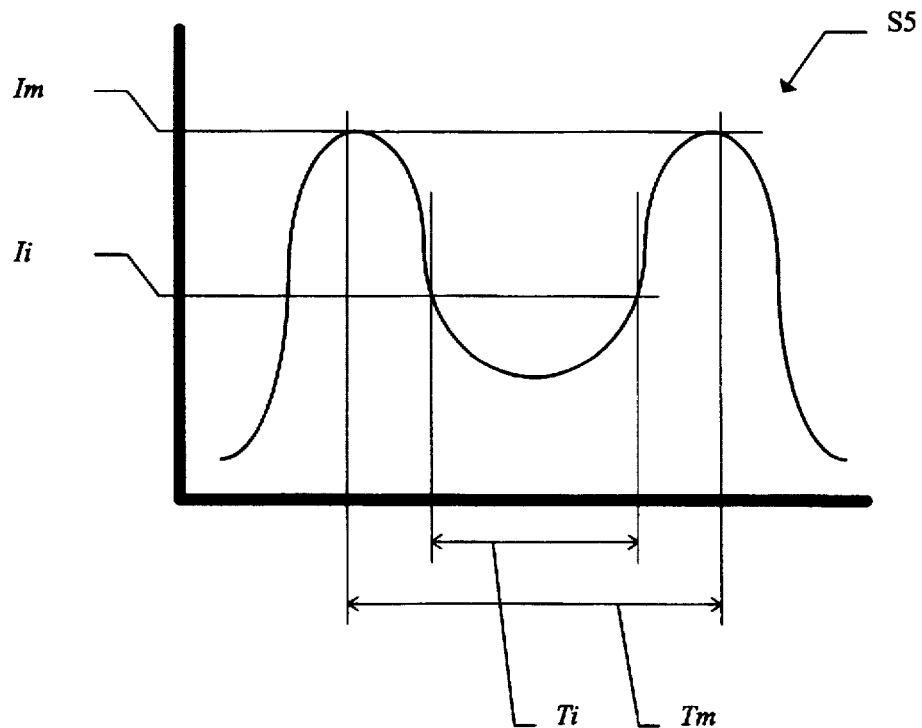

The scattering pattern also provides information for determining the particle's size and velocity. Referring to FIGS. 5(a,b), a particle crossed light beam L along path P5. The corresponding scattering intensity pattern as a function of time S5 shows the expected twin peaks surrounding a reduced intensity inner region. The size of the particle affects the maximum scattered light intensity. As long as the twin peak signal is present and the particle size is not on the order of the wavelength of the light beam, the maximum scattered intensity uniquely determines the particle size.

The interaction between light and particles with diameters on the order of the wavelength of the light can yield multi-valued scattered light functions where the relationship between particle size and scattering intensity is not unique. Present optical measurement systems have this same limitation. In this situation, each particle size will scatter the same, but the amount of scattering may not be unique to a particle size. Forward scattering has been used to reduce this effect. Mie-scatttering theory can also be used to calculate the actual relationship between scattering intensity and particle size. While any electromagnetic beam can function in the present invention, the size determination can be simpler if the wavelength is chosen so to not be on the order of the particle diameter. For example, wavelengths from 190 to 400 nanometers (ultraviolet) and from 400 to 700 nanometers (visible) are suitable for many particle sizes. Sources and detectors for ultraviolet and visible wavelengths are commonly available. Infrared beams (wavelengths over 700 nanometers) are also suitable although the longer wavelength might complicate particle sizing due to multi-valued scattering, as discussed above.

The particle velocity can also be determined from the scattered light. The average particle velocity in the direction normal to the light beam axis is:

$$v = \frac{2Rm}{Tm} \sqrt{\frac{1 - (Ri/Rm)^2}{1 - (Ti/Tm)^2}}$$

where v is the average particle velocity in the direction normal to the light beam axis. Rm is the radial distance from the beam axis to the maximum intensity in the high intensity ring. Tm (in the Figure) is the elapsed time from the first scattered light peak to the second scattered light peak. Ri is the radial position at which the light beam intensity is a selected proportion ($\alpha$) of the maximum light beam intensity. Commercial beam intensity profilers known to those skilled in the art can provide measurements of Rm and Ri.

The two elapsed times, Tm and Ti, are determined from the scattered light detected. Ti (in the Figure) is the elapsed time from when the scattered light intensity Ii is the same proportion ($\alpha$) of the maximum scattered light intensity Im to when the scattered light intensity Ii again reaches the same proportion ($\alpha$) of the maximum scattered light intensity Im. The proportion ($\alpha$) must be between 0 and 1, and can be chosen based on the capabilities of the light beam, light detection, and scattering analysis elements. A high proportionate scattering intensity Ii can make it easier to distinguish particles passing through the reduced intensity region of the light beam from coincident particles and particles passing through edges of the beam. The maximum scattering intensity Im must be higher than the proportionate scattering intensity Ii so that measurements of time and intensity can be made. Both scattering intensities Im, Ii are limited by particle scattering characteristics and by the power input by the light beam. Note that the elapsed times could be measured from points other than the maximum scattering point. If a proportion, $\beta$, of the maximum scattered light was used in place of the maximum scattered light, then the distance to the same proportion of the maximum beam intensity, $\beta$ times Rm, would be used in place of Rm in the discussion above.

The particular sizes and equipment discussed above are cited merely to illustrate a particular embodiment of the invention. It is contemplated that the use of the invention may involve components having different sizes and characteristics. It is intended that the scope of the invention be defined by the claims appended hereto.

We claim:

1. An apparatus for determining one or more properties of a particle, comprising:
    a) light means for generating a light beam having an axis, where the light beam intensity is graduated so that on every path that intersects the light beam axis the light beam intensity at a first point along the path is less than the light beam intensity at second and third points along the path, where the first point is between the second and third points along the path;
    b) direction means for directing the light beam onto the particle;
    c) detection means for detecting light scattered as a result of the light beam illuminating the particle; and
    d) analysis means for determining particle properties from the detected scattered light.

2. The apparatus of claim 1, wherein the direction means comprises a lens to focus the light beam where it will intersect a path of a moving particle.

3. The apparatus of claim 1, wherein the detection means comprises a photodetector.

4. The apparatus of claim 1, wherein the light means comprises a laser.

5. An apparatus for determining one or more properties of a particle, comprising:
    a) light means for generating a light beam having an axis, where the light beam intensity is graduated so that on at least one path through the light beam perpendicular to the light beam axis the light beam intensity at a first point along the path is less than the light beam intensity at second and third points along the path, where the first point is between the second and third points along the path, wherein the light means comprises annular means for generating a light beam having a center, where the light beam has a first intensity at a first radial distance from the center and has a second intensity less than the first intensity and greater than zero at radial distances less than the first radial distance from the center;
    b) direction means for directing the light beam onto the particle;
    c) detection means for detecting light scattered as a result of the light beam illuminating the particle; and
    d) analysis means for determining particle properties from the detected scattered light.

6. The apparatus of claim 5, wherein the annular means comprises a laser.

7. The apparatus of claim 1, wherein the light means is chosen from the group consisting of:
   a) a laser generating a light beam having a propagation axis and an optical fiber having an axis, where the laser is mounted with the optical fiber so that the propagation axis is not parallel to the fiber's axis;
   b) a prism and a laser generating a light beam passing through the prism;
   c) a lens and a laser generating a light beam passing through the lens; and
   d) a laser generating a light beam and mask means for obstructing regions of the light beam.

8. The apparatus of claim 1, wherein the analysis means comprises:
   a) means for determining events where the detected light scattered has a selected intensity profile; and
   b) means for counting the number of events that occur within a selected time interval.

9. The apparatus of claim 1, wherein the analysis means comprises velocity analysis means for determining the velocity of the particle.

10. The apparatus of claim 5, wherein the analysis means comprises velocity analysis means for determining the velocity of the particle, wherein the velocity analysis means comprises:
   a) means for determining a first time corresponding to a first maximum of the detected scattered light;
   b) means for determining a second time corresponding to a second maximum of the detected scattered light;
   c) means for determining a third time after the first time and before the second time corresponding to a first occurrence when the detected scattered light reaches a selected proportion of the maximum detected scattered light; and
   d) means for determining a fourth time after the third time and before the second time corresponding to a second occurrence when the detected scattered light reaches the selected proportion of the maximum detected scattered light.

11. The apparatus of claim 10, wherein the velocity analysis means further comprises means for determining the velocity of the particle as the result of $(2Rm/Tm)$ multiplied by the square root of $((1-(Ri/Rm)^2)/(1-(Ti/Tm)^2))$, where Rm is the distance from the light beam axis to the point of maximum light beam intensity, Tm is the time from the first time to the second time, Ri is the distance from the light beam axis to the point where the light beam intensity is the selected proportion of the maximum light beam intensity, and Ti is the time from the third time to the fourth time.

12. The apparatus of claim 1, wherein the analysis means comprises size analysis means for determining the size of the particle.

13. The apparatus of claim 12, wherein the size analysis means comprises means for determining size of the particle from the maximum intensity of the detected scattered light.

14. The apparatus of claim 5, wherein the analysis means comprises:
   a) means for determining size of the particle from the maximum detected scattered light; and
   b) velocity analysis means comprising:
      i) means for determining a first time corresponding to a first maximum of the detected scattered light;
      ii) means for determining a second time corresponding to a second maximum of the detected scattered light;
      iii) means for determining a third time after the first time and before the second time corresponding to a first occurrence when the detected scattered light reaches a selected proportion of the maximum detected scattered light; and
      iv) means for determining a fourth time after the third time and before the second time corresponding to a second occurrence when the detected scattered light reaches the selected proportion of the maximum detected scattered light.

15. The apparatus of claim 14, wherein the velocity analysis means further comprises means for determining the velocity of the particle as the result of $(2Rm/Tm)$ multiplied by the square root of $((1-(Ri/Rm)^2)/(1-(Ti/Tm)^2))$, where Rm is the distance from the light beam axis to the point of maximum light beam intensity, Tm is the time from the first time to the second time, Ri is the distance from the light beam axis to the point where the light beam intensity is the selected proportion of the maximum light beam intensity, and Ti is the time from the third time to the fourth time.

16. An apparatus for determining the size and velocity of a particle comprising:
   a) annular means for generating a light beam having a center, where the light beam has a first intensity at a first radial distance from the center and has a second intensity less than the first intensity and greater than zero at radial distances less than the first radial distance from the center;
   b) direction means for directing the light beam onto the particle;
   c) detection means for detecting light scattered as a result of the light beam illuminating the particle;
   d) flux means for counting the number of events where the detected light scattered has a selected intensity profile that occur within a selected time interval;
   e) size analysis means for determining size of the particle from the maximum intensity of the detected scattered light; and
   f) velocity analysis means comprising:
      i) means for determining a first time corresponding to a first maximum of the detected scattered light;
      ii) means for determining a second time corresponding to a second maximum of the detected scattered light;
      iii) means for determining a third time after the first time and before the second time corresponding to a first occurrence when the detected scattered light reaches a selected proportion of the maximum detected scattered light; and
      iv) means for determining a fourth time after the third time and before the second time corresponding to a second occurrence when the detected scattered light reaches the selected proportion of the maximum detected scattered light.

17. The apparatus of claim 16, wherein the velocity analysis means comprises means for determining the velocity of the particle as the result of $(2Rm/Tm)$ multiplied by the square root of $((1-(Ri/Rm)^2)/(1-(Ti/Tm)^2))$, where Rm is the distance from the light beam center to the point of maximum light beam intensity, Tm is the time from the first time to the second time, Ri is the distance from the light beam center to the point where the light beam intensity is the selected proportion of the maximum light beam intensity, and Ti is the time from the third time to the fourth time.

18. The apparatus of claim 16, wherein the annular means is chosen from the group consisting of:
   a) a laser generating a light beam having a propagation axis and an optical fiber having an axis, where the laser is mounted with the optical fiber so that the propagation axis is not parallel to the fiber's axis;

b) a prism and a laser generating a light beam passing through the prism;

c) a lens and a laser generating a light beam passing through the lens; and d) a laser generating a light beam and mask means for obstructing regions of the light beam.

19. A method for measuring properties of a particle moving along a path, comprising the steps of:

a) illuminating a portion of the path with a light beam having an axis, and having a graduated intensity so that on every path that intersects the light beam axis the light beam intensity at a first point along the path is less than the light beam intensity at second and third points along the path, where the first point is between the second and third points along the path, b) collecting the light scattered by the particle as it moves along the portion of the path, and c) determining properties of the particle from the collected scattered light.

* * * * *